United States Patent
Hitchen

[11] Patent Number: 6,106,816
[45] Date of Patent: Aug. 22, 2000

[54] STABLE, PEARLY SHAMPOO COMPOSITIONS CONTAINING NON-VOLATILE SILICONE

[75] Inventor: David Andrew Hitchen, South Wirral, United Kingdom

[73] Assignee: Chesebrough-Pond's USA Co., divison of Concopo, Inc., New York, N.Y.

[21] Appl. No.: 08/140,693

[22] Filed: Oct. 21, 1993

Related U.S. Application Data

[63] Continuation of application No. 08/020,004, Feb. 17, 1993, abandoned, which is a continuation of application No. 07/883,237, May 7, 1992, abandoned, which is a continuation of application No. 07/620,503, Nov. 30, 1990, abandoned.

[30] Foreign Application Priority Data

Jun. 20, 1990 [GB] United Kingdom .................. 9013801

[51] Int. Cl.$^7$ .......................... A61K 7/075; A61K 47/32; A61K 47/34
[52] U.S. Cl. ...................................... 424/70.16; 424/70.12
[58] Field of Search ............................ 424/70.12, 70.16, 424/70.19, 70.21, 70.24, 70.27, 70.28, 490; 514/881, 951; 510/122, 123–124, 125, 127

[56] References Cited

U.S. PATENT DOCUMENTS

| | | | |
|---|---|---|---|
| 4,345,080 | 8/1982 | Bolich, Jr. ................... | 424/70 |
| 4,364,837 | 12/1982 | Pader ......................... | 424/70 |
| 4,394,287 | 7/1983 | Scarpelli .................... | 424/70 |
| 4,623,396 | 11/1986 | Kimura et al. ............. | 106/291 |
| 4,711,775 | 12/1987 | Dittmar et al. ............ | 424/70 |
| 4,902,499 | 2/1990 | Bolich, Jr. et al. ........ | 424/47 |

FOREIGN PATENT DOCUMENTS

| | | |
|---|---|---|
| 0018717 | 11/1980 | European Pat. Off. . |
| 0074264 | 3/1983 | European Pat. Off. . |
| 0077920 | 5/1983 | European Pat. Off. . |
| 0170927 | 2/1986 | European Pat. Off. . |
| 0181773 | 5/1986 | European Pat. Off. . |
| 0 400 976 | 12/1990 | European Pat. Off. . |
| 62-004219 | 1/1987 | Japan . |
| 01-121 209 | 5/1989 | Japan . |
| 01-224 310 | 9/1989 | Japan . |
| 2 015 562 | 9/1979 | United Kingdom . |
| 2149806 | 6/1985 | United Kingdom . |

OTHER PUBLICATIONS

Official Patent Gazette of the Japanese Patent Office for JP/90/1804 (Lion).

*Primary Examiner*—Edward J. Webman
*Attorney, Agent, or Firm*—Milton L. Honig

[57] ABSTRACT

An aqueous shampoo composition comprises, in addition to water, a surfactant chosen from anionic, nonionic or amphoteric surfactants, and mixtures thereof;

an insoluble, non-volatile silicone;

a suspending polymer chosen from polyacrylic acid, cross-linked polymers of acrylic acid, copolymers of acrylic acid with a hydrophobic monomer, copolymers of carboxylic acid—containing monomers and acrylic esters, cross-linked copolymers of acrylic acid and acrylate esters, and heteropolysaccharide gums; and titanium dioxide coated mica.

18 Claims, No Drawings

6,106,816

STABLE, PEARLY SHAMPOO COMPOSITIONS CONTAINING NON-VOLATILE SILICONE

This is a continuation application of Ser. No. 08/020,004 filed Feb. 17, 1993, which is a continuation of Ser. No. 07/883,237 filed May 7, 1992, which is a continuation of Ser. No. 07/620,503 filed Nov. 30, 1990, all of which are now abandoned.

BACKGROUND OF THE INVENTION

The present invention relates to shampoo compositions, and more particularly to shampoo compositions containing non-volatile silicone materials which condition the hair leaving it softer and more manageable.

When washing the hair with conventional shampoo compositions, the natural oils are removed together with the dirt and unwanted oils. When too much of the natural oil is removed, for example by especially frequent washing, the hair becomes less easy to comb or style, and subject to static build-up causing "flyaway".

Hair conditioners have been developed to try to restore the condition of the hair. These compositions are normally applied to the hair after shampooing, left on the hair for a period of time and rinsed off. This process is time consuming and expensive since two separate products are needed.

Conditioning shampoos containing cationic conditioning agents have been disclosed for example in EP 18 717 (Unilever). These cationic agents confer some conditioning benefit on the hair, but are often thought to leave a residue on the hair, which may cause dulling on dry hair.

Silicone oils are known to be conditioning agents and their use in conditioning shampoos has been proposed for example in EP 74 264 (Unilever) and EP 77 920 (Kao). However, it has been found that care is needed when formulating silicone containing shampoos as the compositions are often unstable and the silicone oil tends to separate out.

Conventional pearliser materials such as ethylene glycol stearates have been used to suspend silicone materials (EP 181 773, Procter & Gamble). These pearlisers are formed by cooling an aqueous emulsion of liquid ethylene glycol mono- and/or di-stearate, giving rise to a range of waxy crystal leaflets or needles having a range of different sizes and crystal habits. It is difficult to obtain a narrow size distribution, and even when concentrated pearliser pastes are obtained commercially, control of the crystal habit is not assured. Pearliser crystals have been found to separate when incorporated in shampoos with the dual function of pearlising the composition and suspending other materials.

Titanium dioxide coated mica particles on the other hand are free of this problem of instability, in part because the process of manufacture may be regulated to ensure a tighter size distribution, and also because the dry particles may easily be sieved.

SUMMARY OF THE INVENTION

We have found that a stable, pearly shampoo composition comprising insoluble non-volatile silicone may be obtained by including a suspending polymer, as defined below to prevent the silicone "creaming" to the top of the bottle in storage, and also to prevent the particles of titanium dioxide coated mica from settling.

The invention accordingly provides an aqueous shampoo composition comprising in addition to water (a) from 2 to 40% by weight of surfactant chosen from anionic, nonionic or amphoteric surfactant, or mixtures thereof;

(b) from 0.01 to 10% by weight of insoluble, non-volatile silicone;

(c) from 0.1 to 5% by weight of a suspending polymer chosen from polyacrylic acid, cross-linked polymers of acrylic acid, copolymers of acrylic acid with a hydrophobic monomer, copolymers of carboxylic acid—containing monomers and acrylic esters, cross-linked copolymers of acrylic acid and acrylate esters, and heteropolysaccharide gums; and (d) from 0.01 to 5% by weight of titanium dioxide coated mica.

DETAILED DESCRIPTION OF THE INVENTION (a) Surfactant

The composition according to the invention comprises a surfactant chosen from anionic, nonionic or amphoteric surfactant or mixtures thereof.

Suitable anionic surfactants are the alkyl sulphates, alkyl ether sulphates, alkaryl sulphonates, alkyl succinates, alkyl sulphosuccinates, N-alkoyl sarcosinates, and alpha-olefin sulphonates, especially their sodium, magnesium, ammonium and mono-, di- and triethanolamine salts. The alkyl groups generally contain from 8 to 18 carbon atoms and may be unsaturated. The alkyl ether sulphates may contain from one to 10 ethylene oxide or propylene oxide units per molecule, and preferably contain 2 to 3 ethylene oxide units per molecule.

Examples of suitable anionic surfactants include sodium lauryl sulphate, sodium oleyl succinate, ammonium lauryl sulphosuccinate, ammonium lauryl sulphate, sodium dodecylbenzene sulphonate, triethanolamine dodecylbenzene sulphonate and sodium N-lauryl sarcosinate. The most referred anionic surfactants are sodium lauryl sulphate, sodium lauryl ether sulphate 2EO and 3EO, ammonium lauryl sulphate and ammonium lauryl ether sulphate 1EO, 2EO and 3EO.

The nonionic surfactants suitable for use in the composition of the invention may include condensation products of aliphatic ($C_8$–$C_{18}$) primary or secondary linear or branched chain alcohols or phenols with alkylene oxides, usually ethylene oxide and generally 6–30 EO.

Other suitable nonionics include mono or di alkyl alkanolamides or alkyl polyglucosides. Examples include coco mono or diethanolamide, coco mono isopropanolamide, and coco di glucoside.

The amphoteric surfactants suitable for use in the composition of the invention may include alkyl amine oxides, alkyl betaines, alkyl amidopropyl betaines, alkyl mono- or dialkanolamides, alkyl sulphobetaines, alkyl glycinates and alkyl carboxyglycinates, wherein the alkyl groups have from 8 to 18 carbon atoms. Examples include lauryl amine oxide, cocomonoethanolamide, cocodiethanolamide, cocamidopropyl betaine, cocodimethyl sulphopropyl betaine and preferably cocobetaine.

The surfactants are present in the shampoo composition of the invention in an amount of from 2 to 40% by weight, and preferably from 5 to 30% by weight.

If an amount of less than 2% by weight of surfactant is present in the composition, inadequate foaming is achieved, and if more than 40% by weight is present, no further increase in cleansing power or foaming ability is observed.

(b) Silicone

The shampoo composition of the invention also comprises an insoluble, non-volatile silicone, which may be a polyalkyl siloxane, a polyalkylaryl siloxane, or mixtures thereof. The silicone should be insoluble in the matrix of the shampoo.

Suitable polyalkyl siloxanes include polydimethyl siloxanes having a viscosity of from 5 to 100,000 centistokes at 25° C. These siloxanes are available commercially from the General Electric Company as the VISCASIL series and from Dow Corning as the DC 200 series. The viscosity can be measured by means of a glass capillary viscometer as set forth in Dow Corning Corporate Test Method CTMOO04 Jul. 20, 1970.

Also suitable is polydiethyl siloxane.

The polyalkylaryl siloxanes which may be used in the shampoo compositions of the invention include polymethylphenyl polysiloxanes having a viscosity of from 15 to 65 centistokes at 25° C. These siloxanes are available commercially from the General Electric Company as SF 1075 methyl phenyl fluid or from Dow Corning as 556 Cosmetic Grade Fluid.

Also suitable are silicone gums, such as those described in U.S. Pat. No. 4,152,416 (Spitzer), and on General Electric Silicone Rubber product Data Sheet SE 30, SE 33, SE 54 and SE 76. "Silicone gum" denotes polydiorganosiloxanes having a molecular weight of from 200,000 to 1,000,000, and specific examples include polydimethyl siloxane copolymer, polydimethyl siloxane/diphenyl/methylvinylsiloxane copolymer, polydimethylsiloxane/methylvinylsiloxane copolymer and mixtures thereof.

Further examples of insoluble, non-volatile silicones suitable for use in the compositions of the invention are the polyaminofunctional silicones such as DC 929, available from Dow Corning.

By polyaminofunctional silicone is meant polyalkyl or polyalkylaryl siloxane in which the silicone chain is at least partly substituted by —NNR$^1$ wherein R and R$^1$ are the same or different and are H, alkyl or phenyl.

The siloxanes described above may be incorporated directly into the shampoos of the invention or may be added as a preformed emulsion, such as BY22-007 or BY22-022 available from Toray Silicone Co. Limited.

The shampoo compositions of the invention contain from 0.01 to 10% by weight, preferably from 0.5 to 5% by weight, of insoluble, non-volatile silicone. If less than 0.01% by weight is present in the composition, little conditioning benefit is observed, and if more than 10% by weight is present, the hair will appear greasy.

(c) Suspending Polymer

The composition of the invention comprises from 0.1 to 5% by weight, preferably form 0.2 to 3%, of a suspending polymer chosen from polyacrylic acid, cross-linked polymers of acrylic acid, copolymers of acrylic acid with a hydrophobic monomer, copolymers of carboxylic acid—containing monomers and acrylic esters, cross-linked copolymers of acrylic acid and acrylate esters, and heteropolysaccharide gums.

Polyacrylic acid is available commercially as CARBOPOL 420, CARBOPOL 488 or CARBOPOL 493 (Goodrich). Polymers of acrylic acid cross-linked by a polyfunctional agent which are suitable for use in the shampoo compositions of the invention include those available commercially as CARBOPOL 910, CARBOPOL 934, CARBOPOL 940, and CARBOPOL 941 (Goodrich).

An example of a suitable copolymer of a carboxylic acid containing monomer and acrylic esters is CARBOPOL 1342 (Goodrich). Suitable cross-linked polymers of acrylic acid and acylate esters are PEMULEN TR1 or PEMULAN TR2. A suitable heteropolysaccharide gum is xanthan gum, for example that available as KELZAN mu.

The suspending polymers generally have a negative charge in the shampoo system, and will uncoil and take on an extended structure. The suspending polymer stabilises the shampoo of the invention and prevents the titanium dioxide coated mica particles from settling, and the silicone from creaming to the top on standing.

(d) Titanium dioxide coated mica

The shampoo composition of the invention includes particles of titanium dioxide coated mica. These particles may vary in size from 2 to 150 $\mu$m in diameter.

In general, smaller particles give rise to a shampoo composition having a pearly appearance, whereas particles having a larger average diameter will result in a glittery shampoo composition.

Suitable particles are those sold under the trade names TIMIRON (Merck) or FLAMENCO (Mearl). Particularly suitable are:

|  | Average particle size ($\mu$m) |
|---|---|
| TIMIRON MP-45 | 40–100 |
| TIMIRON MP-47 | 15–130 |
| TIMIRON MP-148 | 25–150 |
| TIMIRON MP-111 | 25–100 |
| TIMIRON MP-1001 | 5–20 |
| TIMIRON MP-1005 | <15 |
| FLAMENCO REFINA | 3–20 |
| FLAMENCO VELVET | 5–20 |
| FLAMENCO SATINA | 5–25 |
| FLAMENCO PEARL | 10–35 |

The shampoo compositions of the invention comprise from 0.01 to 5%, preferably from 0.05 to 3% by weight of titanium dioxide coated mica.

Cationic Conditioning Agent

The shampoo composition of the invention may also further comprise a cationic conditioning agent.

Suitable cationic conditioning agents include the cationic cellulose ethers described in U.S. Pat. Nos. 3,816,616 and 4,272,515 and which are available commercially from Union Carbide Corporation as POLYMER JR. Other suitable materials are the cationic polygalactomannan gum derivatives describes in U.S. Pat. No. 4,298,494 which are commercially available under the trade mark JAGUAR from Celanese-Stein Hall. An example of a suitable material has the CTFA designation guar hydroxypropyltrimonium chloride and is available under the the name JAGUAR C13S, which has a degree of substitution of the cationic groups of about 0.13. Other suitable materials include that known as JAGUAR C17 (degree of substitution of about 0.25 to 0.31), and JAGUAR C16 which is hydroxypropylated cationic guar derivative containing hydroxypropyl substituent groups as well as cationic quaternary ammonium groups. In JAGUAR C16, the degree of substitution is 0.11 to 0.16 and the moles of substitution of hydroxypropyl groups is 0.8 to 1.1.

Other cationic conditioning agents useful in the shampoos of the present invention include cationic polyamide polymers such as the low molecular weight adipic acid/diethylene-triamine polyamide and the copolymers of vinylpyrrolidone and dimethylaminoethyl methacrylate quaternised with dimethyl sulphate (GAFQUAT 755, GAF Corporation) described in U.S. Pat. No. 4,080,310; the graft cationic copolymer containing N-vinylpyrrolidone, dimethylaminoethyl methacrylate and polyethylene glycol described in U.S. Pat. No. 4,048,301; the mineral acid salts of the amino-alkyl esters of homo- and copolymers of unsaturated carboxylic acids having from 3 to 5 carbon atoms described in U.S. Pat. No. 4,009,256; and the polymers of etherified starch described in U.S. Pat. No. 3,186,911.

The high molecular weight polymers sold under the trade mark MERQUAT by Merck & Co. Inc., are cationic polymers which are also suitable for use in the present shampoos. Representative ones are MERQUAT 100, a highly charged cationic dimethyldiallylammonium chloride homopolymer, and MERQUAT 550, a highly charged cationic copolymer prepared with dimethyldiallylammonium chloride and acrylamide. These materials are designated in the CFTA dictionary as Quaternium-40 and Quaternium-41, respectively.

Cationic surfactants such as mono-, di- and tri-alkyl quaternary ammonium salts may also be used as the cationic conditioning agent in the shampoos of the invention. Suitable examples are cetyl trimethylammonium chloride, cetyl trimethylammonium bromide and stearyltrimethylammonium chloride.

The cationic conditioning agent is preferably present in the shampoo composition of the invention in an amount of from 0.01 to 5% by weight, most preferably in an amount of from 0.2 to 3% by weight.

Other Pearlising Agents

The shampoo of the invention can also optionally include a pearlising agent in addition to titanium dioxide-coated mica. Examples of other pearlising agents include ethyleneglycol monostearate, ethylene glycol di-stearate, polyethylene glycol di-stearate (especially PEG-3 di-stearate) and mixtures thereof, in an amount of from 0.01 to 20%, preferably 0.01–0.5% by weight of the shampoo.

It is to be noted that the disadvantages alluded to earlier of using pearlising agents such as those exemplified above are largely overcome when titanium dioxide-coated mica is present as the principle pearlising agent. Antidandruff Agents The shampoo of the invention can also optionally include an antidandruff agent chosen from zinc pyrithione, 1-hydroxy-2-pyridone (a preferred example of which is OCTOPIROX) and mixtures thereof, in an amount of from 0.01 to 20%, preferably 0.1 to 10% by weight of the shampoo.

Other Ingredients

The shampoo of the invention may also include minor amounts of other ingredients such as antibacterial agents, foam boosters, pearlescers, perfumes, dyes, colouring agents, preservatives, thickeners, proteins, polymers, phosphate esters and buffering agents. Use of the Composition The composition of the invention is intended to be used as a shampoo. The hair is wet in the normal manner, an amount of the shampoo composition, generally about 5 ml, is applied to the wet hair, rubbed to obtain a lather. The lather is rinsed from the hair, and shampoo may be reapplied as before, if necessary.

EXAMPLES

The invention is further illustrated by the following Examples. Where a mixture of ammonium lauryl sulphate and ammonium lauryl ether sulphate is used in the following Examples, the approximate ratio of ALS:ALES is 3:1.

Example 1

|  | % wt |
| --- | --- |
| Ammonium lauryl sulphate/ Ammonium lauryl ether sulphate | 8.00 |
| Cocodiethanolamide | 3.00 |
| IONOL butyl hydroxytoluene (BHT) | 0.05 |
| BRIPHOS 03D [1] | 1.05 |
| Hydrolysed silk protein | 0.10 |
| CARBOPOL 1342 | 0.40 |
| Polyethoxylated lanolin | 0.30 |
| JAGUAR C13S | 0.30 |
| TIMIRON MP-1005 | 0.06 |
| Triethanolamine | 0.80 |
| Silicone emulsion (50%) [2] | 6.00 |
| Perfume, preservative | qs |
| Water to | 100 |

[1] BRIPHOS 03D is a mixture of esters of phosphoric acid and the polyethylene glycol ether of oleyl alcohol.
[2] Silicone emulsion comprises 50% by weight silicone oil (60,000 cs), 4% by weight cetostearyl alcohol and 25% by weight SLES 2EO.

The ammonium lauryl sulphate/ammonium lauryl ether sulphate and the BHT were heated in the main vessel to 75° C. to melt the BHT, with constant stirring.

CARBOPOL 1342 was dispersed with stirring in 50% of the water, and the resulting dispersion added to the main vessel.

The polyethoxylated lanolin was melted at 70 to 75° C. and added to the main vessel.

The cocodiethanolamide and BRIPHOS 03D were added to the main vessel with stirring.

JAGUAR C13S was dispersed in 35% of the water and added to the main vessel with high shear mixing.

Preservative, hydrolysed silk protein, triethanolamine and perfume were added to the main vessel, followed by the silicone emulsion, and finally the TIMIRON MP-1005.

The shampoo composition of Example 1 was found to be stable at 0° C. and at ambient temperature after 6 months storage. Some separation was seen after storage at 37° C. and 45° C. for 4 months.

Example 2

|  | % wt |
| --- | --- |
| Ammonium lauryl sulphate/ Ammonium lauryl ether sulphate | 8.00 |
| Cocodiethanolamide | 3.00 |
| BHT | 0.05 |
| BRIPHOS 03D | 1.05 |
| Hydrolysed silk protein | 0.10 |
| Xanthan gum | 0.40 |
| Polyethoxylated lanolin | 0.30 |
| JAGUAR C13S | 0.30 |
| TIMIRON MP-1005 | 0.06 |
| Triethanolamine | 0.80 |
| Silicone emulsion (50%) of Example 1 | 6.00 |
| Perfume, preservative | qs |
| Water to | 100 |

The ALS/ALES mixture was placed in the main vessel.

JAGUAR C13S was dispersed in 90% of the water, and added to the main vessel with high shear mixing.

The polyethoxylated lanolin was melted and added to the main vessel.

Cocodiethanolamide and BRIPHOS 03D were mixed and added slowly to the main vessel. The xanthan gum was added with mixing. The hydrolysed silk protein and triethanolamine were added. The preservative was added. The BHT was dissolved in the perfume and added to the main vessel.

The silicone emulsion was added, followed by the TIMIRON MP-1005, with rapid stirring.

The shampoo composition of Example 2 was found to be stable at 0° C., at ambient temperature and at 37° C. after storage for 6 months.

Example 3

| | % wt |
|---|---|
| Ammonium lauryl sulphate/ | 8.00 |
| Ammonium lauryl ether sulphate | |
| Polyethoxylated lanolin | 0.30 |
| CARBOPOL 1342 | 0.40 |
| Cocodiethanolamide | 3.00 |
| BRIPHOS 03D | 1.05 |
| BHT | 0.05 |
| JAGUAR C13S | 0.30 |
| Hydrolysed silk protein | 0.10 |
| Triethanolamine | 0.80 |
| TIMIRON MP-1005 | 0.06 |
| TORAY BY-22022 [3] | 6.00 |
| Perfume, preservative | qs |
| Water to | 100 |

[3.] TORAY BY-22022 is a commercially available silicone emulsion (50% by weight silicone oil).

The ALS/ALES mixture and BHT were added to the main vessel and heated to melt the BHT. The hydrolysed silk protein was added. CARBOPOL 1342 was dispersed in 50% of the water and added to the main vessel with stirring. Cocodiethanolamide was added very slowly, followed by BRIPHOS 03D.

JAGUAR C13S was dispersed in 45% of the water and added to the main vessel with high shear mixing, Triethanolamine and hydrolysed silk protein were added followed by perfume and preservative. The silicone emulsion was then added, and finally TIMIRON MP-1005 was added with stirring.

The shampoo composition of Example 3 was found to be stable at 0° C., after storage for 6 months.

Example 4

| | % wt |
|---|---|
| Ammonium lauryl sulphate/ | 8.00 |
| Ammonium lauryl ether sulphate | |
| Polyethoxylated lanolin | 0.30 |
| CARBOPOL 1342 | 0.40 |
| Cocodiethanolamide | 3.00 |
| BRIPHOS 03D | 1.05 |
| BHT | 0.05 |
| JAGUAR C13S | 0.30 |
| Hydrolysed silk protein | 0.10 |
| Triethanolamine | 0.80 |
| TIMIRON MP-45 | 0.06 |
| Silicone emulsion of Example 1 | 6.00 |
| Perfume, preservative | qs |
| Water to | 100 |

A shampoo composition was made according to the method of Example 1.

The shampoo composition of Example 4 was found to be stable after storage for 6 months at 0° C., ambient temperature, 37° C. and 45° C.

Example 5

| | % wt |
|---|---|
| Ammonium lauryl sulphate/ | 8.00 |
| Ammonium lauryl ether sulphate | |
| Polyethoxylated lanolin | 0.30 |
| Xanthan gum | 0.40 |
| Cocodiethanolamide | 3.00 |
| BRIPHOS 03D | 1.05 |
| BHT | 0.05 |
| JAGUAR C13S | 0.30 |
| Hydrolysed silk protein | 0.10 |
| TIMIRON MP-111 | 0.30 |
| Silicone emulsion of Example 1 | 6.00 |
| Perfume, preservative | qs |
| Water to | 100 |

The shampoo composition of Example 5 was found to stable after 6 months storage at 0° C. and at ambient temperature. Slight separation was seen after storage at 37° C. for 6 months and at 45° C. for 3 months.

Example 6

A shampoo composition using the following ingredients, the methods of Example 3, replacing cocodiethanolamide with cocamidopropyl betaine, and ALS/ALES with sodium lauryl ether sulphate 3E0.

| | % wt |
|---|---|
| Sodium lauryl ether sulphate 2E0 | 10.00 |
| Cocamidopropyl betaine | 4.00 |
| Polyethoxylated lanolin | 0.30 |
| JAGUAR C13S | 0.30 |
| BRIPHOS 03D | 1.05 |
| TIMIRON MP-111 | 0.06 |
| CARBOPOL 1342 | 0.40 |
| Hydrolysed silk protein | 0.10 |
| BHT | 0.05 |
| TORAY BY-22022 | 4.00 |
| Perfume, preservative | qs |
| Water to | 100 |

Example 7

A shampoo composition was prepared using the following ingredients, according to the method of claim 6.

| | % wt |
|---|---|
| Sodium lauryl ether sulphate 2E0 | 10.00 |
| Cocamidopropyl betaine | 4.00 |
| Polyethoxylated lanolin | 0.30 |
| JAGUAR C13S | 0.30 |
| BRIPHOS 03D | 1.05 |
| TIMIRON MP-111 | 0.06 |
| PEMULEN TR1 | 0.40 |
| Hydrolysed silk protein | 0.10 |
| BHT | 0.05 |
| TORAY BY-22022 | 4.00 |
| Perfume, preservative | qs |
| Water to | 100 |

Example 8

A shampoo is prepared with the following ingredients:

| | % wt |
|---|---|
| Ammonium lauryl sulphate/ Ammonium lauryl ether sulphate | 8.00 |
| Cocamidopropyl betaine | 6.50 |
| CARBOPOL 940 | 0.40 |
| JAGUAR C13S | 0.15 |
| Propylene glycol | 0.50 |
| Silicone emulsion of Example 1 | 4.00 |
| BHT | 0.05 |
| TIMIRON MP-1001 | 0.20 |
| Perfume, preservative | qs |
| Water to | 100 |

Example 9

A shampoo is prepared with the following ingredients:

| | % wt |
|---|---|
| Ammonium lauryl sulphate/ Ammonium lauryl ether sulphate | 8.00 |
| Cocamidopropyl betaine | 6.50 |
| CARBOPOL 940 | 0.40 |
| JAGUAR C13S | 0.15 |
| Propylene glycol | 0.50 |
| Silicone emulsion of Example 1 | 4.00 |
| Zinc pyrithione | 1.00 |
| BHT | 0.05 |
| TIMIRON MP-1001 | 0.20 |
| Ethylene glycol di-stearate | 0.10 |
| Perfume, preservative | qs |
| Water to | 100 |

Example 10

A shampoo is prepared with the following ingredients:

| | % wt |
|---|---|
| Ammonium lauryl sulphate/ Ammonium lauryl ether sulphate | 8.00 |
| Cocamidopropyl betaine | 6.50 |
| CARBOPOL 940 | 0.40 |
| JAGUAR C13S | 0.15 |
| Propylene glycol | 0.50 |
| Silicone emulsion of Example 1 | 4.00 |
| OCTOPIROX | 1.00 |
| BHT | 0.05 |
| TIMIRON MP-1001 | 0.20 |
| Perfume, preservative | qs |
| Water to | 100 |

Example 11

A shampoo is prepared with the following ingredients:

| | % wt |
|---|---|
| Ammonium lauryl sulphate/ Ammonium lauryl ether sulphate | 8.00 |
| Cocamidopropyl betaine | 6.50 |
| CARBOPOL 940 | 0.40 |
| JAGUAR C13S | 0.15 |
| Propylene glycol | 0.50 |
| Silicone emulsion of Example 1 | 4.00 |
| OCTOPIROX | 1.00 |
| Zinc pyrithione | 1.00 |
| BHT | 0.05 |
| TIMIRON MP-1001 | 0.20 |
| Perfume, preservative | qs |
| Water to | 100 |

What is claimed is:

1. An aqueous conditioning shampoo composition comprising, in addition to water:
   (a) from 2 to 40% by weight of surfactant selected from the group consisting of anionic, nonionic and amphoteric surfactants, and mixtures thereof;
   (b) from 0.01 to 10% by weight of insoluble, non-volatile silicone which conditions hair;
   (c) from 0.01 to 3% by weight of titanium dioxide coated mica particles dispersed in the shampoo matrix; and
   (d) from 0.2 to 3% by weight of a crosslinked acrylic acid polymer for suspending the dispersed titanium dioxide coated mica particles and preventing them from settling in the composition as well as the insoluble, non-volatile silicone conditioning agent from creaming to the top of the composition on standing.

2. A shampoo composition as claimed in claim 1, wherein the anionic surfactant is selected from the group consisting of sodium lauryl ether sulphate 2EO, sodium lauryl ether sulphate 3EO, ammonium lauryl sulphate, ammonium lauryl ether sulphate 1EO, ammonium lauryl ether sulphate 2EO, ammonium lauryl ether sulphate 3EO and mixtures thereof.

3. A shampoo composition as claimed in claim 2, wherein the amphoteric surfactant is selected from the group consisting of $C_{8-18}$ alkyl amidopropyl betaine and $C_{8-18}$ alkyl betaine.

4. A shampoo composition as claimed in claim 3, wherein the amphoteric surfactant is cocobetaine.

5. A shampoo composition as claimed in claim 1, wherein the insoluble, non-volatile silicone is selected from the group consisting of polyalkyl siloxanes, polyalkylaryl siloxanes, and mixtures thereof.

6. A shampoo composition as claimed in claim 5, wherein the insoluble, non-volatile silicone is selected from the group consisting of polydimethyl siloxane, polymethylphenyl siloxane and mixtures thereof.

7. A shampoo composition as claimed in claim 1, wherein the titanium dioxide coated mica has an average particle size of from 2 to 150 μm in diameter.

8. A shampoo composition as claimed in claim 1, which additionally comprises a cationic conditioning agent.

9. A shampoo composition as claimed in claim 8, wherein the cationic conditioning agent is present in an amount of from 0.01 to 5% by weight.

10. A shampoo composition as claimed in claim 9 wherein the cationic conditioning agent is selected from the group consisting of a cationic cellulose, a cationic guar gum and mixtures thereof.

11. A shampoo composition as claimed in claim 10, wherein the cationic guar gum is guar hydroxypropyltrimonium chloride.

12. A shampoo composition as claimed in claim 1, which further comprises a pearlising agent selected from the group consisting of ethylene glycol mono-stearate, ethylene glycol di-stearate, polyethyleneglycol di-stearate and mixtures thereof.

13. A shampoo composition as claimed in claim 1, which further comprises an antidandruff agent selected from the group consisting of zinc pyrithione, 1-hydroxy-2-pyridone and mixtures thereof.

14. An aqueous conditioning shampoo composition comprising, in addition to water:

(a) from 2 to 40% by weight of lauryl ether sulphate;

(b) from 0.01 to 10% by weight of insoluble, nonvolatile silicone which conditions hair;

(c) from 0.01 to 3% by weight of titanium dioxide-coated mica particles dispersed in the shampoo matrix;

(d) from 0.2 t0 3% by weight of a crosslinked acrylic acid polymer for suspending the dispersed titanium dioxide coated mica particles and preventing them from settling in the composition as well as the insoluble non-volatile silicone conditioning agent from creaming to the top of the composition on standing; and (e) a perfume present in an effective amount to provide a fragrance to the shampoo composition.

15. An aqueous conditioning shampoo composition comprising, in addition to water:

(a) from 2 to 40% by weight of surfactant selected from the group consisting of anionic, nonionic and amphoteric surfactants, and mixtures thereof;

(b) from 0.01 to 10% by weight of insoluble, non-volatile silicone which conditions hair;

(c) from 0.01 to 3% by weight of titanium dioxide coated mica particles dispersed in the shampoo matrix; and (d) from 0.2 to 3% by weight of a xanthan gum for suspending the dispersed titanium dioxide coated mica particles and preventing them from settling in the composition as well as the insoluble, non-volatile silicone conditioning agent from creaming to the top of the composition on standing.

16. A shampoo composition as claimed in claim 15 wherein the anionic surfactant is a lauryl ether sulphate.

17. A shampoo composition as claimed in claim 16, wherein the amphoteric surfactant is selected from the group consisting of $C_{8-8}$ alkyl amidopropyl betaine and $C_{8-18}$ alkyl betaine.

18. A shampoo composition as claimed in claim 17, further comprising from 0.01 to 5% by weight of a cationic guar gum.

* * * * *